United States Patent [19]
Suga et al.

[11] Patent Number: 5,882,631
[45] Date of Patent: Mar. 16, 1999

[54] ORAL COMPOSITION

[75] Inventors: Yoshio Suga, Osaka; Yuka Ogawa, Kyoto, both of Japan

[73] Assignee: Sunstar Inc., Osaka, Japan

[21] Appl. No.: 65,609

[22] Filed: Apr. 24, 1998

[30] Foreign Application Priority Data

| Apr. 24, 1997 | [JP] | Japan | 9-123403 |
| Jun. 3, 1997 | [JP] | Japan | 9-161807 |
| Feb. 27, 1998 | [JP] | Japan | 10-063971 |

[51] Int. Cl.⁶ ..................... A61K 7/16
[52] U.S. Cl. ................... 424/49
[58] Field of Search .......... 424/49–58

[56] References Cited

U.S. PATENT DOCUMENTS

| 4,976,736 | 12/1990 | White et al. | 623/16 |
| 5,084,051 | 1/1992 | Türmala et la. | 606/77 |
| 5,292,495 | 3/1994 | Nakajima et al. | 423/432 |
| 5,302,396 | 4/1994 | Phadke et al. | 424/465 |
| 5,437,873 | 8/1995 | Phadke et al. | 424/465 |
| 5,480,827 | 1/1996 | Guillemin et al. | 435/240.23 |
| 5,711,957 | 1/1998 | Patat et al. | 424/422 |

*Primary Examiner*—Shep K. Rose
*Attorney, Agent, or Firm*—Sughrue, Mion, Zinn, Macpeak & Seas, PLLC

[57] ABSTRACT

Oral compositions containing a water-insoluble noncationic bactericide showing improved stability with time and improved rheologic properties, and exerting excellent effects of eliminating dental plaque, preventing halitosis and eliminating tooth-staining substances.

Addition of porous calcium carbonate to the oral compositions makes it possible to prevent the decrease in the bactericidal activity of water-insoluble noncationic bactericides such as triclosan and improve the stability thereof while exerting excellent effects of eliminating dental plaque, preventing halitosis and eliminating tooth-staining substances. Furthermore, addition of sodium carboxymethyl cellulose to the oral compositions makes it possible to improve rheologic properties and stability with time.

9 Claims, No Drawings

ORAL COMPOSITION

FIELD OF THE INVENTION

This invention relates to oral compositions showing stabilized bactericidal activity of water-insoluble noncationic bactericides when packed in containers having the innermost layer made of synthetic resins. More particularly, it relates to oral compositions exerting excellent effects of suppressing thixotropic properties and variation in viscosity at a high temperature, and preventing solid-liquid separation in stability with time, and further exerting excellent effects of eliminating dental plaque, preventing halitosis and eliminating tooth-staining substances.

BACKGROUND OF THE INVENTION

It has been pointed out that dental plaque adsorbed onto teeth is an important factor causing gingivitis. To eliminate the dental plaque, it has been a practice to physically cleaning the oral cavity by brushing, etc. However, it takes a long time to clean the oral cavity by brushing and the dental plaque-controlling effect thus achieved is still insufficient.

Under these circumstances, studies have been made to develop oral compositions such as dentifrices containing bactericides so as to achieve supplemental effects of eliminating the dental plaque. In particular, it is known that cationic bactericides are efficacious in preventing the formation of dental plaque. However, cationic bactericides can be hardly processed into preparations due to the poor compatibility with other components in compositions. To overcome this problem, it has been recently proposed to add water-insoluble noncationic bactericides (triclosan, etc.), which are highly compatible with other components in compositions, to oral compositions.

When compositions containing such water-insoluble noncationic bactericides are packed in containers made of synthetic resins, however, the stability of these bactericides is lowered with the passage of time and the bactericidal effects are deteriorated due to the adsorption of the bactericides onto the inner wall of the containers, etc.

To solve this problem, JP-A-20288820, JP-A-6-92830 and JP-A-6-279248 propose to prevent the adsorption of nonionic bactericides onto containers by improving the containers, for example, with the use of specific polymers as the innermost layer of the containers (the term "JP-A" as used herein means an "unexamined published Japanese patent application").

On the other hand, JP-A-8-198623 discloses that porous calcium carbonate having excellent properties of absorbing oil and water has been developed and are usable as a food additive. However, it has never been proposed so far to use this porous calcium carbonate in oral compositions for stabilizing bactericides, eliminating dental plaque, perverting halitosis, etc.

SUMMARY OF THE INVENTION

An object of the present invention is to provide oral compositions wherein the stability with time and the bactericidal activity of water-insoluble noncationic bactericides are not deteriorated even with the use of commonly employed synthetic resin materials such as polyethylene, and wherein by further compounding sodium carboxymethyl cellulose having an average degree of etherification of 0.5 to 1.8, thixotropic properties and variation in viscosity at a high temperature are suppressed, and rough skin and solid-liquid separation in stability with time are prevented.

Another object of the present invention is to provide oral compositions for eliminating dental plaque, preventing halitosis and eliminating tooth-staining substances.

To achieve the above-mentioned objects, the present inventors have conducted extensive studies and, as a result, found out that oral compositions containing porous calcium carbonate and water-insoluble noncationic bactericides have elevated stability with time of the water-insoluble noncationic bactericide, owing to the effect of the porous calcium carbonates, and exhibit improved effects in rheologic properties and stability with time as a preparation and exhibit improved effects of eliminating dental plaque, preventing halitosis and eliminating tooth-staining substances, by compounding sodium carboxymethyl cellulose having an average degree of etherification of 0.5 to 1.8. The present invention has been completed based on this finding.

In the present invention, the improvement in rheologic properties and stability with time as a preparation means that thixotropic properties and variety in viscosity at a high temperature are suppressed and rough skin and solid-liquid separation in stability with time are prevented.

DETAILED DESCRIPTION OF THE INVENTION

The porous calcium carbonate to be used in the present invention is porous precipitated calcium carbonate with a high purity and a high porosity wherein secondary particles have been formed by, e.g., multi-stage carboxylation of chained fine particles, different from heavy calcium carbonate forming no secondary particles, ultrafine precipitated calcium carbonate particles (e.g., having a primary particle size of 0.02 to 0.08 $\mu$m) or the conventional precipitated calcium carbonate forming secondary particles by natural aggregation. It is available as, for example, PORECAL-N (manufactured by Shiraishi Calcium K.K.).

It is preferable that the porous calcium carbonate to be used in the present invention has an primary particle diameter of from 0.05 to 0.5 $\mu$m, more preferably from 0.1 to 0.5 $\mu$m, a bulk density of from 0.05 to 0.8 g/ml and a BET specific surface area of from 15 to 100 m$^2$/g, though the present invention is not restricted thereto. The porous calcium carbonate to be used in the present invention preferably has a secondary particle diameter of from 1 to 5 $\mu$m.

The porous calcium carbonate to be used in the present invention may be produced by multi-stage carboxylation of chained fine particles e.g., as described in JP-A-8-198623.

The content of the porous calcium carbonate in the oral composition of the present invention may range from 0.1 to 40% by weight, preferably from 0.5 to 10% by weight. When the content of porous calcium carbonate is less than 1% by weight, the stability of the water-insoluble noncationic bactericide tends not to be sufficiently elevated. When the content thereof exceeds 40% by weight, on the other hand, the effects tend not to be improved any more.

The water-insoluble noncationic bactericide to be used in the present invention is at least one compound selected from among halogenated diphenyl ethers, halogenated salicylanilides, halogenated carboanilides, p-hydroxybenzoic acid esters and phenol compounds.

Examples of the halogenated diphenyl ethers include 2',4,4'-trichloro-2-hydroxy-diphenyl ether (triclosan) and 2,2'-dihydroxy-5,5'-dibromo-diphenyl ether. Examples of the halogenated salicylanilides include 4',5-dibromosalicylanilide, 3,4',5-trichlorosalicylanilide, 2,3,3', 5-tetrachlorosalicylanilide and 3,5-dibromo-3'-trifluoromethylsalicylanilide. Examples of the halogenated carboanilides include 3,4,4'-trichlorocarboanilide and 3-trifluoromethyl-4,4'-dichlorocarboanilide. Examples of the p-hydroxybenzoic acid esters include methyl p-hydroxybenzoate, ethyl p-hydroxybenzoate, propyl p-hydroxybenzoate and butyl p-hydroxybenzoate. Examples of the phenol compounds include isopropylmethyl phenol.

Among these water-insoluble noncationic bactericides, halogenated diphenyl ethers are preferable and triclosan (2',4,4'-trichloro-2-hydroxy-diphenyl ether) is particularly preferable therefor. In the present invention, the content of the water-insoluble noncationic bactericide may range from 0.001 to 3% by weight, preferably from 0.01 to 1% by weight, based on the whole composition. When the content of the water-insoluble noncationic bactericide is less than 0.001% by weight, sufficient bactericidal effect tends not to be achieved. When the content thereof exceeds 3% by weight, on the other hand, the resultant composition tends to become irritative to the oral mucosa, which results in a problem in practice.

To the oral compositions to be used in the present invention, at least one sodium carboxymethyl cellulose preferably having an average degree of etherification of from 0.5 to 1.8. The lower limit of the average degree of etherification of the sodium carboxymethyl cellulose is preferably 0.6, more preferably 0.8. The upper limit of the average degree of etherification of the sodium carboxymethyl cellulose is preferably 1.5. Especially, sodium carboxymethyl celluloses having different average degrees of etherification of from 0.8 to 1.1 and from 1.2 to 1.5 are preferably compounded to the present oral compositions.

When the degree of etherification is less than 0.5, the rheologic properties and stability with time tend not to be improved sufficiently. When the degree of etherification exceeds 1.8, the firmness tend not to be kept.

The sodium carboxymethyl cellulose to be used in the present invention may be compounded in an amount of from 0.1 to 5.0 wt %, preferably 0.5 to 3.0 wt % based on the total amount of the oral composition. When the content of the sodium carboxymethyl cellulose is less than 0.1 wt %, it tends to be difficult to suppress the solid-liquid separation. When the content of the sodium carboxymethyl cellulose is more than 5 wt %, the oral composition tends to be solidified.

The oral compositions of the present invention may be processed into toothpastes, powdery dentifrices, liquid dentifrices, ointments, dermatological pastes, chewing gums, etc. Among all, toothpastes are preferable from a practical viewpoint. These compositions can be packed into any commonly employed resin containers made of, for example, polyolefin resins (polyethylene, polypropylene, etc.) and polyester, polyethylene terephthalate, polycarbonate, polystyrene, polyamide and polyvinyl chloride resins in the form of single-layered tubes, laminate tubes, bottles, jars, etc.

In addition to the essential (and additional) components as described above, the oral compositions of the present invention may further contain appropriate components commonly employed in the art, so long as the effects of the present invention are not deteriorated thereby.

In the case of toothpastes, for example, use may be made of abrasive agents such as calcium carbonate, calcium phosphate, calcium secondary phosphate, calcium pyrophosphate, insoluble sodium metaphosphate, titanium dioxide, amorphous silica, crystalline silica, alumino silicate, aluminum oxide, aluminum hydroxide, resin, hydroxyapatite, etc. either singly or as a mixture of two or more thereof. The content of these components generally ranges from 10 to 60% by weight based on the whole composition.

Examples of anionic surfactants usable as foaming agents or detergents include sodium alkylsulfates (sodium laurylsulfate, sodium myristylsulfate, etc.), sodium N-acylsarcosinates (sodium N-lauroylsarcosinate, sodium N-myristoylsarcosinate, etc.), N-acylglutamic acid salts (sodium N-palmitoylglutamate, etc.), and sulfosuccinic acid surfactants (polyoxyethylene alkyl disodium sulfosuccinate, dialkyl sodium sulfosuccinate, etc.).

Examples of nonionic surfactants usable herein include sugar fatty acid esters (sucrose fatty acid ester, maltose fatty acid ester, lactose fatty acid ester, etc.), polyoxyethylene alkyl ethers, fatty acid alkanolamides, polyoxyethylene sorbitan fatty acid esters (polyoxyethylene sorbitan monolaurate, polyoxyethylene sorbitan monostearate, etc.), polyoxyethylene fatty acid esters (polyoxyethylene-hardened castor oil, etc.), sorbitan fatty acid esters, fatty acid monoglycerides and polyoxyethylene/polyoxypropylene block copolymers.

Examples of amphoteric surfactants usable herein include N-alkyldiaminoethylglycine (N-lauryldiaminoethylglycine, N-myristyldiethylglycine, etc.), N-alkyl-N-carboxymethylammonium betaine, 2-alkyl-1-hydroxyethylimidazoline betaine sodium and lauryldimethylaminoacetic acid betaine. Either one of these surfactants or a mixture of two or more thereof may be employed. The content thereof preferably ranges from 0.1 to 10% by weight based on the whole composition.

As a thickener other than sodium carboxymethyl cellulose, use can be made of cellulose derivatives (hydroxyethyl cellulose, etc.), alkali metal alginates (sodium alginate, etc.), gums (carrageenan, xanthan gum, tragacanth gum, acacia, etc.), synthetic thickeners (polyvinyl alcohol, sodium polyacrylate, etc.), inorganic thickeners (silica gel, aluminum silica gel, bee gum, etc.), etc. Either one of these thickeners or a mixture of two or more thereof may be used. The content thereof usually ranges from 0.1 to 10% by weight based on the whole composition.

As a humectant, use can be made of sorbitol, glycerin, ethylene glycol, propylene glycol, 1,3-butylene glycol, polyethylene glycol, polypropylene glycol, xylitol, maltitol, lactitol, etc. Either one of these humectants or a mixture of two or more thereof may be used. The content thereof usually ranges from 5 to 70% by weight based on the whole composition.

As a pH-balanced agent, use can be made of citric acid, phosphoric acid, malic acid, pyrophosphoric acid, lactic acid, tartaric acid, glycerophosphoric acid, acetic acid, nitric acid, silicic acid, chemically available salts thereof, sodium hydroxide, etc. Either one of these pH-balanced agents or a mixture of two or more thereof may be used so as to adjust the pH value of the composition to 5 to 9. The content thereof usually ranges from 0.01 to 2% by weight based on the whole composition.

Moreover, the oral compositions of the present invention may contain flavors such as menthol, carvone, eugenol, methyleugenol, methyl salicylate, methyl eugenol, thymol, anethole, limonene, ocimene, n-decyl alcohol, citronellol, α-terpineol, methyl acetate, citronenyl acetate, cineol, linalol, ethyllinalol, vanillin, thyme, nutmeg, spearmint oil, peppermint oil, lemon oil, orange oil, sage oil, rosemary oil, cinnamon oil, Labiatae oil, winter green oil, clove oil, eucalyptus oil and piment oil. Either one of these flavors or a mixture of two or more thereof may be used. The content thereof ranges from 0.1 to 5% by weight, preferably from 0.5 to 2% by weight, based on the whole composition.

Moreover, the oral compositions of the present invention may contain sweeteners such as saccharin sodium, acesulfame potassium, stevioside, neohesperidyl dihydrochalcone, glycyrrhizin, perillartine, thaumatin, aspartylphenylalanyl methyl ester and xylitol. The content of the sweeteners ranges from 0.01 to 1% by weight, preferably from 0.05 to 0.5% by weight, based on the whole composition.

The oral compositions of the present invention may furthermore contain medicinal components other than the water-insoluble noncationic bactericides, for example, vitamin E analogs (dl-α-tocopherol acetate, tocopherol succinate, tocopherol nicotinate, etc.), cationic bactericides (chlorhexidine hydrochloride, cetylpyridinium chloride, benzethonium chloride, etc.), amphoteric bactericides (dodecyldiaminoethylglycine, etc.), enzymes (dextranase, amylase, protease, mutanase, lysozyme, lytic enzymes, etc.), alkali metal monofluorophosphates (sodium monofluorophosphate, potassium monofluorophosphate, etc.), fluorides (sodium fluoride, stannous fluoride, etc.), tranexamic acid, epsilon-aminocaproic acid, aluminum chlorohydroxylallantoin, dihydrocholesterol, glycyrrhizin salts, glycyrrhizinic acid, glycerophosphate, chlorophyll, sodium chloride, caropeptide and water soluble inorganic phosphoric acid compounds. Use can be made of either one of these components or a mixture of two or more thereof.

To further illustrate the present invention in greater detail, and not by way of limitation, the following Examples will be given. In these Examples, all contents are expressed in % by weight.

[TEST EXAMPLE]

1. Evaluation of stability of noncationic bactericide
(1) Preparation of sample

Toothpastes of the following compositions were each prepared in a conventional manner and packed in a laminate tube having polyethylene at the innermost layer. After storing at 40° C. for 1 month, the residual rate of triclosan and the bactericidal effect were evaluated by the methods as will be described hereinbelow.

| Component | Content (%) |
|---|---|
| porous calcium carbonate | given in Table 1 |
| heavy calcium carbonate | " |
| anhydrous silica | 3.0 |
| sorbitol | given in Table 1 |
| sodium carboxymethyl cellulose | given in Table 1 |
| sodium lauryl sulfate | given in Table 1 |
| nonionic surfactant | " |
| saccharin sodium | 0.1 |
| flavor | 1.0 |
| water insoluble noncationic bactericide | 0.3 |
| purified water | the balance |
| total | 100.0. |

(2) Method for measuring residual rate of water-insoluble noncationic bactericide Next, the method for measuring the residual rate of the water-insoluble noncationic bactericide will be described with the use of triclosan as an example.

(Method for measuring residual rate of triclosan)

20 ml of methanol was added to each toothpaste (2.5 g) prepared above. The resultant mixture was stirred for 20 minutes to thoroughly disperse the methanol in the toothpaste and then centrifuged at 17,000 rpm for 10 minutes to give the supernatant. The residue was further subjected to the same treatment twice and the supernatants were combined. Then methanol was added thereto to give a total volume of 100 ml. By using the resultant mixture as a sample, triclosan was determined by liquid chromatography. The residual rate of triclosan was determined in accordance with the following formula (1) and evaluated based on the criteria given below.

Formula (1):

$$\text{Residual rate (\%)} \frac{\text{triclosan content after 1 month}}{\text{triclosan content at preparation}} \times 100$$

Criteria:

○: Triclosan residual rate ≧ 90%.

x: Triclosan residual rate < 90%.

(Bactericidal activity test)

To 5 ml of a 4-fold slurry of a toothpaste was added 0.1 ml of a suspension ($10^8$–$10^9$ CFU/ml) of *Streptococcus mutans*. After incubating at 37° C. for 3 minutes, the sample solution was inoculated on a tripticase/soy/agar (TSA) plate and incubated under anaerobic conditions ($N_2/H_2/CO_2$=85/10/5) at 37° C. for 2 days followed by the measurement of the minimum bactericidal concentration (%; hereinafter referred to simply as "MBC"). As a standard, use was made of a 0.05% aqueous solution of triclosan (solubilized with a small amount of SLS). The evaluation was made based on the following criteria.

Criteria:

○: The MBC of the sample is comparable to the MBC of the standard or lower.

x: The MBC of the sample is higher than that of the standard.

Table 1 summarizes the data of the triclosan residual rate and the results of the bactericidal activity test.

As Table 1 clearly shows, the invention products containing porous calcium carbonate are improved in stability with time and sustain the bactericidal activity, compared with the comparative ones.

TABLE 1

| Component | Example (%) 1 | 2 | 3 | 4 | 5 | 6 | 7 | Comp. Example (%) 1 | 2 | 3 |
|---|---|---|---|---|---|---|---|---|---|---|
| porous calcium carbonate[1] | 0.1 | 40.0 | 10.0 | 2.0 | 7.0 | 5.0 | 5.0 | — | — | — |
| heavy calcium carbonate | 35.0 | — | 20.0 | 25.0 | 20.0 | 35.0 | 35.0 | 30.0 | — | — |
| calcium phosphate | — | — | — | — | — | — | — | 10.0 | 40.0 | — |
| anhydrous silica | 3.0 | 3.0 | 3.0 | 3.0 | 3.0 | 3.0 | 3.0 | 3.0 | 3.0 | 8.0 |
| triclosan | 0.001 | 3.0 | 1.0 | 0.5 | 0.5 | 0.5 | 0.5 | 0.5 | 0.5 | 0.5 |
| sorbitol | 35.0 | 35.0 | 35.0 | 35.0 | 35.0 | 35.0 | 10.0 | 35.0 | 35.0 | 35.0 |
| sodium carboxymethyl cellulose[2] | 2.0 | 2.0 | 2.0 | 2.0 | 2.0 | 2.0 | 2.0 | 2.0 | 2.0 | 2.0 |
| sodium lauryl sulfate | 2.0 | 0.2 | 2.0 | 2.0 | 2.0 | 2.0 | 2.0 | 2.0 | 2.0 | 2.0 |
| saccharin sodium | 0.1 | 0.1 | 0.1 | 0.1 | 0.1 | 0.1 | 0.1 | 0.1 | 0.1 | 0.1 |
| flavor | 1.0 | 1.0 | 1.0 | 1.0 | 1.0 | 1.0 | 1.0 | 1.0 | 1.0 | 1.0 |
| purified water | the balance | the balance | the balance | the balance | the balance | the balance | the balance | the balance | the balance | the balance |
| total | 100.0 | 100.0 | 100.0 | 100.0 | 100.0 | 100.0 | 100.0 | 100.0 | 100.0 | 100.0 |
| Evaluation: | | | | | | | | | | |
| residual rate of nonionic bactericide | ○ | ○ | ○ | ○ | ○ | ○ | ○ | X | X | X |
| bactericidal activity | ○ | ○ | ○ | ○ | ○ | ○ | ○ | X | X | X |

Porous calcium carbonate[1]: average primary particle diameter 0.2 μm, bulk density 0.5 g/ml, and BET specific surface area 23 m$^2$
Sodium carboxymethyl cellulose[2]: degree of etherification 1.2

2. Dental plaque-eliminating model test (1) Preparation of sample

Toothpastes having the following compositions were prepared in a conventional manner and employed in the evaluation.

| Component | Content (%) |
|---|---|
| powdery component | given in Table 2 |
| sorbitol | 40.0 |
| sodium carboxymethyl cellulose (degree of etherification 1.2) | 2.0 |
| sodium lauryl sulfate | 1.5 |
| Pluronic-type surfactant (POE200 POP40) | 5.0 |
| saccharin sodium | 1.0 |
| flavor | 1.0 |
| purified water | the balance |
| total | 100.0. |

(2) Evaluation

As a model of dental plaque, use was made of a 1 mg/ml solution (pH 7, in Veronal buffer solution) of water-insoluble glucan produced by S. mutans ATCC25175 strain. 0.5 g portions of the toothpastes (invention product and comparative ones) shown in Table 2 were each mixed with 3 ml of the above-mentioned solution of insoluble glucan. After shaking for 30 minutes, the mixture was centrifuged and the supernatant was removed. The residue was subjected to color development of reducing sugar by the phenol-sulfuric acid method and the absorbance was measured at 490 nm. A calibration curve was formed by the phenol-sulfuric acid method in the same manner with the use of the water-insoluble glucan solution described above and the amount of glucan adsorbed by the powder was determined therefrom. Then the adsorption rate was calculated by referring the initial amount of the added glucan as to 100.

As Table 2 shows, the oral composition containing porous calcium carbonate of Example 3 is superior in the capability of adsorbing glucan to the product containing common precipitated calcium carbonate of Comparative Example 4 or that containing common heavy calcium carbonate of Comparative Example 5. That is to say, the oral composition of the present invention is appropriate for eliminating dental plaque.

3. Halitosis prevention model test 4 g portions of 4-fold slurries of the toothpastes of Example 8 and Comparative Example 4 as given in Table 2 were sampled and sealed in glass vials. 0.5 ml of a 2 μg/ml solution of methylmercaptan in ethanol was injected into each vial followed by lightly shaking at 37° C. for 10 minutes. Then 5 ml of the head space gas was taken up and the methylmercaptan contained therein was determined by gas chromatography. By using a calibration curve of methylmercaptan, the concentration was determined and the deodorization rate (%) was calculated by referring the initial amount of the added methylmercaptan as to 100.

As Table 2 shows, the invention product is superior in the deodorizing effect to the comparative one. It is therefore recognized that the oral composition is useful in preventing halitosis, since the porous calcium carbonate adsorbs halitosis components and thus eliminate the same (deodorization).

4. Tooth-staining substance elimination model test

As a model of tooth-staining substances, use was made of a purple solution containing 0.5% of tea polyphenol and 0.5% of iron (III) citrate ammonium. 0.5 g portions of the toothpastes (invention product and comparative ones) shown in Table 2 were each mixed with 5 ml of the tooth-staining substance model solution as described above.

After shaking for 30 minutes, the mixture was centrifuged and the absorbance of the supernatant was measured at 300 nm. The adsorption rate was calculated in accordance with the following formula:

$$\text{Adsorption rate (\%)} = \frac{A - [\text{absorbance of supernatant after applying sample}]}{A} \times 100$$

A: Absorbance of the tooth-staining substance model solution.

As Table 2 shows, the invention product is superior in the effect of eliminating the tooth-staining substances to the comparative ones. It is therefore recognized that the oral composition containing porous calcium carbonate is useful in eliminating the tooth-staining substances.

TABLE 2

|  | Ex. 8 | Comp. Ex. 4 | Comp. Ex. 5 |
|---|---|---|---|
| Powdery component content (%) |  |  |  |
| porous calcium carbonate[2] (average secondary particle diameter: 3.5 μm) | 5 | — | — |
| precipitated calcium carbonate[3] (secondary particles: not formed) | — | 35 | — |
| heavy calcium carbonate[4] (secondary particles: not formed) | 30 | — | 35 |
| Evaluation |  |  |  |
| dental plaque-control (adsorption rate of insoluble glucan: %) | 28 | 16 | 11 |
| halitosis prevention (methylmercaptan deodorization rate: %) | 42 | — | 30 |
| tooth-staining substance-elimination (polyphenol + iron adsorption rate: %) | 41 | 20 | — |

TABLE 2-continued

|  | Ex. 8 | Comp. Ex. 4 | Comp. Ex. 5 |
|---|---|---|---|
| Porous calcium carbonate[2]: |  |  |  |
| average primary particle diameter 0.3 μm, bulk density 0.4 g/ml, and BET specific surface area 23 m² |  |  |  |
| Precipitated calcium carbonate[3]: |  |  |  |
| average primary particle diameter 1 μm, bulk density 0.4 g/ml, and BET specific surface area 5 m² |  |  |  |
| Heavy calcium carbonate[4]: |  |  |  |
| average primary particle diameter 5 μm, bulk density 1.0 g/ml, and BET specific area 1 m² |  |  |  |

5. Evaluation of stability with time and rheologic properties of preparations.

Toothpastes shown in Table 3 below were prepared according to the conventional procedures and were filled in laminate tubes. The stability with time after the storage of one month at 40° C. of the obtained samples was evaluated by the following criteria.

(Evaluation criteria of stability with time)
A: No change
B: Slight phase separation
C: Phase separation and difficulty in practical use
D: Rough skin and solidification (Evaluation criteria of rheological properties)
A: No change
B: Slight high thixotropy
C: High thixotropy
D: Extreme drop in viscosity at 40° C. or more

TABLE 3

| | Example (wt %) | | | | | | | Comp. Example (wt %) | | | | |
|---|---|---|---|---|---|---|---|---|---|---|---|---|
| Component | 9 | 10 | 11 | 12 | 13 | 14 | 15 | 1 | 2 | 3 | 4 | 5 |
| porous calcium carbonate[1] | 0.5 | 40.0 | 10.0 | 2.0 | 7.0 | 5.0 | 5.0 | 5.0 | 5.0 | 5.0 | 5.0 | 5.0 |
| heavy calcium carbonate | 35.0 | — | 20.0 | 25.0 | 20.0 | 35.0 | 35.0 | 30.0 | 20.0 | 20.0 | 20.0 | 20.0 |
| sorbitol | 35.0 | 35.0 | 35.0 | 35.0 | 35.0 | 35.0 | 35.0 | 35.0 | 35.0 | 35.0 | 35.0 | 35.0 |
| sodium carboxymethyl cellulose (degree of etherification) | | | | | | | | | | | | |
| 0.2 | — | — | — | — | — | — | — | — | 0.5 | — | 0.5 | — |
| 0.4 | — | — | — | 0.3 | — | — | — | 0.5 | — | 0.5 | — | — |
| 0.8 | 0.5 | — | — | 0.5 | 0.2 | 0.3 | — | — | — | — | — | — |
| 1.2 | — | 0.5 | — | — | — | 0.3 | 0.5 | — | — | — | — | — |
| 1.5 | — | — | 0.5 | — | 0.5 | 0.3 | — | — | — | — | — | — |
| xanthan gum | — | — | — | — | — | — | — | — | — | 1.0 | — | — |
| carrageenan | — | — | — | — | — | 1.0 | — | — | — | — | 1.0 | 3.0 |
| sodium lauryl sulfate | 2.0 | 2.0 | 1.5 | 1.5 | 1.0 | 1.0 | 0.5 | — | 1.0 | 1.5 | 1.5 | 1.5 |
| saccharin sodium | 0.1 | 0.1 | 0.1 | 0.1 | 0.1 | 0.1 | 0.1 | 0.1 | 0.1 | 0.1 | 0.1 | 0.1 |
| POE(200) · POP(40) block copolymer | — | — | — | — | 0.5 | 0.5 | 1.0 | 2.0 | 0.5 | — | — | — |
| flavor | 0.5 | 0.1 | 0.2 | 1.0 | 0.1 | 0.5 | 0.5 | 0.5 | 0.2 | 0.8 | 1.8 | 2.8 |
| purified water | the balance | the balance | the balance | the balance | the balance | the balance | the balance | the balance | the balance | the balance | the balance | the balance |
| total | 100.0 | 100.0 | 100.0 | 100.0 | 100.0 | 100.0 | 100.0 | 100.0 | 100.0 | 100.0 | 100.0 | 100.0 |
| Evaluation | | | | | | | | | | | | |
| stability with time | B | A | A | A | A | A | A | D | D | C | D | D |
| rheologic properties | A | B | B | A | A | A | B | B | B | B | A | A |
| overall evaluation | ○ | ○ | ○ | ○ | ◎ | ◎ | ○ | X | X | X | X | X | porous calcium carbonate[1]: average primary particle diameter of 0.2 μm, bulk density 0.5 g/ml, and BET specific surface area 23 m²

As is clear from the results of Table 3, improvement in stability with time and rheological properties is confirmed in the working examples where porous calcium carbonate and sodium carboxymethyl cellulose having a degree of etherification of from 0.5 to 1.8 were compounded, compared to the comparative examples.

[EXAMPLE 16]

A toothpaste of the following composition was prepared in a conventional manner and packed in the same laminate tube as the one described above.

| Component | Content (%) |
| --- | --- |
| porous calcium carbonate | 30.0 |
| (average primary particle diameter: 0.2 μm, bulk density: 0.5 g/ml, BET specific surface area: 23 m$^2$) | |
| aluminum hydroxide | 5.0 |
| sorbitol | 20.0 |
| xylitol | 5.0 |
| sodium carboxymethyl cellulose | 1.5 |
| (degree of etherification: 1.3) | |
| sodium lauryl sulfate | 1.5 |
| saccharin sodium | 0.1 |
| flavor | 0.9 |
| triclosan | 0.1 |
| purified water | the balance |
| total | 100.0 |

[EXAMPLE 17]

A toothpaste of the following composition was prepared in a conventional manner and packed in the same laminate tube as the one described above.

| Component | Content (%) |
| --- | --- |
| porous calcium carbonate | 6.0 |
| (average primary particle diameter: 0.08 μm, bulk density: 0.4 g/ml, BET specific surface area: 35 m$^2$) | |
| calcium phosphate | 25.0 |
| sorbitol | 30.0 |
| propylene glycol | 5.0 |
| sodium carboxymethyl cellulose | 1.2 |
| (degree of etherification: 1.0) | |
| sodium N-lauroylsarcosinate | 1.5 |
| sodium monofluorophosphate | 0.5 |
| stevioside | 0.1 |
| flavor | 0.9 |
| isopropylmethyl phenol | 0.5 |
| polyoxyethylene (200)/polyoxypropylene (70) block copolymer | 1.0 |
| purified water | the balance |
| total | 100.0 |

[EXAMPLE 18]

A toothpaste of the following composition was prepared in a conventional manner and packed in the same laminate tube as the one described above.

| Component | Content (%) |
| --- | --- |
| porous calcium carbonate | 20.0 |
| (average primary particle diameter: 0.1 μm, bulk density: 0.2 g/ml, BET specific surface area: 60 m$^2$) | |
| sorbitol | 25.0 |
| sodium carboxymethyl cellulose | 1.5 |
| (degree of etherification: 0.8) | |
| sodium lauryl sulfate | 1.5 |
| saccharin sodium | 0.1 |
| flavor | 0.9 |
| ethyl p-hydroxybenzoate | 0.1 |
| triclosan | 0.2 |
| sodium fluoride | 0.2 |
| polyoxyethylene (200)/polyoxypropylene (70) block copolymer | 2.0 |
| purified water | the balance |
| total | 100.0 |

[EXAMPLE 19]

A liquid dentifrice of the following composition was prepared in a conventional manner and packed in a PET resin container.

| Component | Content (%) |
| --- | --- |
| anhydrous silica | 20.0 |
| porous calcium carbonate | 0.5 |
| (average primary particle diameter: 0.05 μm, bulk density: 0.1 g/ml, BET specific surface area: 90 m$^2$) | |
| sorbitol | 25.0 |
| glycerin | 12.0 |
| carrageenan | 1.0 |
| sodium lauryl sulfate | 1.5 |
| sodium benzoate | 0.2 |
| saccharin sodium | 0.1 |
| flavor | 0.5 |
| triclosan | 0.3 |
| dl-α-tocopherol acetate | 0.5 |
| polyoxyethylene (150)/polyoxypropylene (35) block copolymer | 1.5 |
| sodium silicate | 0.5 |
| purified water | the balance |
| total | 100.0 |

[EXAMPLE 20]

A toothpaste of the following composition was prepared in a conventional manner and packed in the same laminate tube as the one described above.

| Component | Content (%) |
| --- | --- |
| porous calcium carbonate | 6.0 |
| (average primary particle diameter: 0.3 μm, bulk density: 0.4 g/ml, BET specific surface area: 25 m$^2$) | |
| calcium phosphate | 25.0 |
| sorbitol | 30.0 |
| propylene glycol | 5.0 |
| sodium carboxymethyl cellulose | 1.2 |
| (degree of etherification: 1.2) | |
| sodium N-lauroylsarcosinate | 1.5 |
| sodium monofluorophosphate | 0.5 |
| stevioside | 0.1 |
| flavor | 0.9 |

-continued

| Component | Content (%) |
|---|---|
| polyoxyethylene (200)/polyoxypropylene (70) block copolymer | 1.0 |
| purified water | the balance |
| total | 100.0 |

[EXAMPLE 21]

A chewing gum of the following composition was prepared in a conventional manner.

| Component | Content (%) |
|---|---|
| gum base | 28.0 |
| porous calcium carbonate (average primary particle diameter: 0.3 μm, bulk density: 0.4 g/ml, BET specific surface area: 25 m²) | 0.5 |
| xylitol | 40.0 |
| reducing maltose syrup | 26.5 |
| flavor | 5.0 |
| total | 100.0 |

[EXAMPLE 22]

A liquid dentifrice of the following composition was prepared in a conventional manner and packed in a PET resin container.

| Component | Content (%) |
|---|---|
| porous calcium carbonate (average primary particle diameter: 0.2 μm, bulk density: 0.5 g/ml, BET specific surface area: 23 m²) | 0.5 |
| precipitated calcium carbonate | 30.0 |
| sorbitol | 35.0 |
| sodium carboxymethyl cellulose (degree of etherification: 1.8) | 0.5 |
| sodium lauryl sulfate | 1.5 |
| saccharin sodium | 0.1 |
| POE (200)/POP (40) block copolymer | 1.0 |
| flavor | 0.9 |
| triclosan | 0.1 |
| purified water | the balance |
| total | 100.0 |

[EXAMPLE 23]

A toothpaste of the following composition was prepared in a conventional manner and packed in the same laminate tube as the one described above.

| Component | Content (%) |
|---|---|
| porous calcium carbonate (average primary particle diameter: 0.2 μm, bulk density: 0.5 g/ml, BET specific surface area: 23 m²) | 5.0 |
| heavy calcium phosphate | 30.0 |
| sorbitol | 35.0 |
| sodium carboxymethyl cellulose (degree of etherification: 1.8) | 0.5 |

| Component | Content (%) |
|---|---|
| sodium carboxymethyl cellulose (degree of etherification: 0.6) | 0.3 |
| sodium lauryl sulfate | 1.5 |
| saccharin sodium | 0.1 |
| POE (200)/POP (40) block copolymer | 1.0 |
| flavor | 0.9 |
| triclosan | 0.1 |
| purified water | the balance |
| total | 100.0 |

The oral compositions prepared in the above Examples 16 to 19 show high stability with time and highly stable bactericidal activity of the water-insoluble noncationic bactericides such as triclosan. The oral compositions of Examples 16 to 23 are efficacious in eliminating dental plaque, preventing halitosis and eliminating tooth-staining substances.

The present invention provides oral compositions having improved stability with time of water-insoluble noncationic bactericides in containers with the innermost layer made of synthetic resins, showing stabilized bactericidal activity, suppressing thixotropic properties and variation in viscosity at a high temperature, preventing solid-liquid separation in stability with time, and being efficacious in eliminating dental plaque, preventing halitosis and eliminating tooth-staining substances.

What is claimed is:

1. An oral composition comprising toothpaste, liquid dentifrice, or chewing gum containing porous calcium carbonate.

2. An oral composition comprising toothpaste, liquid dentifrice, or chewing gum containing porous calcium carbonate and a water-insoluble noncationic bactericide.

3. The oral composition as claimed in claim 2, wherein said water-insoluble noncationic bactericide is at least one compound selected from the group consisting of halogenated diphenyl ethers, halogenated salicylanilides, halogenated carboanilides, p-hydroxybenzoic acid esters and phenol compounds.

4. The oral composition as claimed in claim 2, wherein said water-insoluble noncationic bactericide is 2',4,4'-trichloro-2-hydroxy-diphenyl ether (triclosan).

5. The oral composition as claimed in claim 1, wherein said porous calcium carbonate has an average primary particle diameter of from 0.05 to 0.5 μm, a bulk density of from 0.05 to 0.8 g/ml and a BET specific surface area of from 15 to 100 m²/g.

6. The oral composition as claimed in claim 1, which further comprises at least one sodium carboxymethyl cellulose having an average degree of etherification of from 0.5 to 1.8.

7. The oral composition as claimed in claim 2, which further comprises at least one sodium carboxymethyl cellulose having an average degree of etherification of from 0.5 to 1.8.

8. The oral composition as claimed in claim 6, wherein the amount of said at least one sodium carboxymethyl cellulose is from 0.1 to 5 wt % based on the oral composition.

9. The oral composition as claimed in claim 7, wherein the amount of said at least one sodium carboxymethyl cellulose is from 0.1 to 5 wt % based on the oral composition.

* * * * *